United States Patent [19]

Tessier et al.

[11] Patent Number: 4,602,038
[45] Date of Patent: Jul. 22, 1986

[54] INSECTICIDAL CYCLOPROPANE CARBOXYLATES

[75] Inventors: Jean Tessier, Vincennes; Jean-Pierre Demoute, Montreuil-sous-Bois; Joseph Cadiergue, Aulnay-sous Bois, all of France

[73] Assignee: Roussel Uclaf, Paris, France

[21] Appl. No.: 618,596

[22] Filed: Jun. 8, 1984

[30] Foreign Application Priority Data

Jun. 14, 1983 [FR] France ................ 83 09810

[51] Int. Cl.$^4$ .............. A01N 53/00; C07C 121/75
[52] U.S. Cl. .................. 514/521; 514/351; 514/471; 514/519; 546/300; 549/496; 558/407; 558/434
[58] Field of Search ............ 260/465 D, 464; 549/496; 546/330, 300; 542/426; 424/304; 514/351, 471, 519, 521

[56] References Cited

U.S. PATENT DOCUMENTS 4,325,969  4/1982  Brown ................ 424/304

FOREIGN PATENT DOCUMENTS 0003420  8/1979  European Pat. Off. .
0008867  3/1980  European Pat. Off. .
2099810  1/1985  United Kingdom .

Primary Examiner—Dolph H. Torrence
Attorney, Agent, or Firm—Bierman, Peroff & Muserlian

[57] ABSTRACT

Novel cyclopropane carboxylates in all isomeric forms of the formula

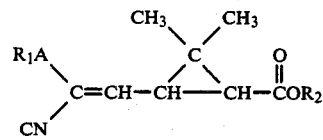

wherein A is selected from the group consisting of —O—, —S—,

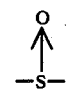

and —SO$_2$—, R$_1$ is selected from the group consisting of optionally unsaturated alkyl of 1 to 18 carbon atoms optionally containing at least one heteroatom in the carbon chain and optionally substituted with at least one halogen, aryl of 6 to 18 carbon atoms and aralkyl of 7 to 18 carbon atoms and R$_2$ is selected from the group consisting of hydrogen, optionally unsaturated alkyl of 1 to 12 carbon atoms, optionally unsaturated cycloalkyl of 3 to 12 carbon atoms and residue of other alcohols used in pyrethrinoids having pesticidal activity for combatting insects, acariens of vegetables and warm-blooded animals and nematodes and novel intermediates.

15 Claims, No Drawings

INSECTICIDAL CYCLOPROPANE CARBOXYLATES

STATE OF THE ART

British Pat. No. 2,099,810 and published European patent applications No. 8,867 and 3,420 disclose various 2,2-dimethyl-cyclopropane carboxylates having a vinyl side chain.

OBJECTS OF THE INVENTION

It is an object of the invention to provide the novel compounds of formula I and novel intermediates therefor.

It is another object of the invention to provide novel pesticidal compositions and to provide a novel method of combatting pests.

These and other objects and advantages of the invention will become obvious from the following detailed description.

THE INVENTION

The novel compounds of the invention are cyclopropane carboxylates in all isomeric forms of the formula $$R_1A\diagdown{C=CH-CH}\diagup^{CN} \diagdown{CH-COR_2}$$ (with gem-dimethyl cyclopropane)  I wherein A is selected from the group consisting of —O—, —S—, $$-\overset{O}{\underset{\uparrow}{S}}-$$

and —SO$_2$—, R$_1$ is selected from the group consisting of optionally unsaturated alkyl of 1 to 18 carbon atoms optionally containing at least one heteroatom in the carbon chain and optionally substituted with at least one halogen, aryl of 6 to 18 carbon atoms and aralkyl of 7 to 18 carbon atoms and R$_2$ is selected from the group consisting of hydrogen, optionally unsaturated alkyl of 1 to 12 carbon atoms, optionally unsaturated cycloalkyl of 3 to 12 carbon atoms and residue of other alcohols used in pyrethrinoids.

Examples of R$_2$ are methyl, ethyl, propyl, isopropyl and linear and branched butyl, pentyl, and hexyl; cyclopropyl, cyclobutyl, cyclopentyl and cyclohexyl; 1-propenyl, 1-butynyl, 1,3-butandienyl and 1-pentenyl; 1-cyclobutynyl, 1-cyclopentadienyl and 1-cyclohexenyl.

When R$_2$ is the residue of an alcohol used in pyrethrinoid synthesis, it is preferably selected from the group consisting of $$-\underset{Z}{\overset{|}{C}H}-Ar, \quad CH_3-\text{(cyclopentenone with CH}_2\text{-CH=CH}_2\text{ side chain)}$$

$$-CH_2-\text{(furan)}-CH_2-\text{(phenyl)} \quad \text{and} \quad -\underset{Y_1}{\overset{|}{C}H}-\underset{}{\overset{Y_2}{C}}=\underset{}{\overset{Y_3}{C}}-Y_4,$$

Z is selected from the group consisting of hydrogen, ethynyl and —CN, Ar is selected from the group consisting of phenyl, pentafluorophenyl (tolyl), (phenoxyphenyl), (2-fluoro-phenoxyphenyl), (pyridyloxyphenyl) and (biphenyl ether with B and X substituents), B is hydrogen or fluorine, X is fluorine, chlorine or bromine, Y$_1$ is selected from the group consisting of hydrogen, fluorine, chlorine, bromine, —C≡N and —C≡CH, Y$_2$, Y$_3$ and Y$_4$ are individually selected from the group consisting of hydrogen, fluorine, chlorine, bromine, alkyl of 1 to 8 carbon atoms and cycloalkyl of 3 to 8 carbon atoms optionally substituted by one or more functional groups, alkenyl of 2 to 8 carbon atoms and alkynyl of 2 to 8 carbon atoms and Y$_2$, Y$_3$ and Y$_4$ can form rings between any two of them.

Examples of R$_1$ are methyl, ethyl, isopropyl, propyl and linear or branched butyl, pentyl or hexyl; cyclopropyl, cyclobutyl, cyclopentyl and cyclohexyl; 1-propenyl, 1-butenyl, 1,3-butadienyl and 1-pentenyl; 1-cyclobutenyl, 1-cyclopentenyl and 1-cyclohexenyl;

—CH$_2$—O—CH$_3$, —CH$_2$—CH$_2$—O—CH$_3$, —CH$_2$—NH—CH$_3$, —CH$_2$—CH$_2$NH—CH$_3$, —CH$_2$—S—CH$_3$,

—CH$_2$—CH$_2$—S—CH$_3$, —CH(Cl)—CH$_2$—CH$_2$(Cl),

—CH(Cl)—CH$_2$—CH(Cl)—CH$_2$—CH$_2$(Cl),

—CH$_2$—CH(Cl)—CH$_2$—CH(Cl)—CH$_3$, —CH$_2$—CH(Br)—CH$_3$,

—CH(Br)—CH$_2$—CH(Br)—CH$_3$ and —CH$_2$—CH(Br)—CH$_2$—CH(Br)—CH$_3$.

R$_1$ may also be phenyl, tolyl, xylyl, or benzyl,

—CH$_2$—CH$_2$—(phenyl), —CH$_2$—CH$_2$—CH$_2$—(phenyl).

When $Y_2$, $Y_3$ or $Y_4$ is a linear, branched or cyclic alkyl radical optionally substituted by at least one functional group, it is preferably methyl, ethyl, isopropyl, n-butyl, isobutyl or tert-butyl optionally substituted by one or more functional groups, and by functional group, it is understood to be halogen, —OH or —SH, —OR' or SR' wherein R' is alkyl of 1 to 8 carbon atoms, —NO$_2$,

wherein R'' and R'' are individually selected from the group consisting of hydrogen and alkyl of 1 to 8 carbon atoms, —C≡N, —SO$_3$H or —PO$_4$H$_2$ or —COAlK$_1$, —SO$_2$AlK$_2$ or —SO$_3$AlK$_3$ in which AlK$_1$, AlK$_2$ and AlK$_3$ are alkyl of 1 to 18 carbon atoms. When $Y_2$, $Y_3$ or $Y_4$ is alkenyl, it is preferably vinyl, allyl or 2-butenyl. When $Y_2$, $Y_3$ or $Y_4$ is alkynyl, it is preferably ethynyl, propargyl or 2-butynyl.

The compounds of formula I can exist in numerous stereoisomeric forms and in effect, they possess two asymmetric carbons in positions 1- and 3- of the cyclopropane and also offer a possibility of E/Z isomery at the double bond as well as one or more possibilities of isomery in the alcohol part.

Among the preferred compounds of formula I are those wherein A is oxygen and especially compounds of the formula

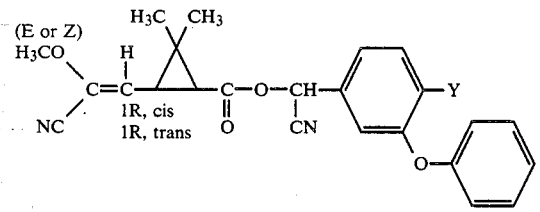

wherein Y is hydrogen or fluorine and especially compounds of the formula

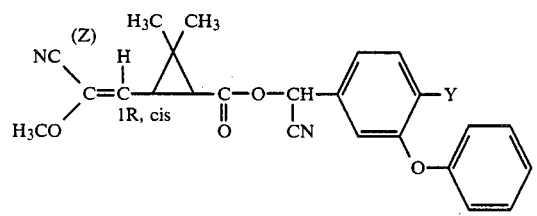

wherein Y is hydrogen or fluorine.

Among specific preferred compounds of formula I are (S)-α-cyano-3-phenoxy-benzyl) (1R,cis,ΔE) 3-(2-methoxy-2-cyanoethenyl)-2,2-dimethyl-cyclopropane carboxylate; (S)α-cyano-3-phenoxy-benzyl) (1R,cis,ΔZ) 3-(2-methoxy-2-cyanoethenyl)-2,2-dimethyl-cyclopropane carboxylate; (S)α-cyano-3-phenoxy-4-fluorobenzyl (1R,cis,ΔZ) 3-(2-methoxy-2-cyanoethenyl)-2,2-dimethyl-cyclopropane carboxylate; 2,3,4,5,6-pentafluorobenzyl (1R,cis,ΔZ) 3-(2-methoxy-2-cyanoethenyl)-2,2-dimethyl-cyclopropane carboxylate; and (S)α-cyano-3-phenoxy-benzyl (1R,trans,ΔE) 3-(2-methoxy-2-cyanoethenyl)-2,2-dimethyl-cyclopropane carboxylate.

The novel process of the invention for the preparation of a compound of formula I comprises reacting a dialkyl α-cyano-α-AR$_1$-methylphosphonate of the formula

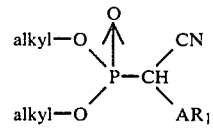

wherein A and R$_1$ have the above definitions and alkyl is alkyl of 1 to 8 carbon atoms or the two alkyl radicals together represent an aliphatic chain optionally substituted by alkyl in an organic solvent with 2,2-dimethyl-3-formylcyclopropane-1-carboxylic acid of the formula

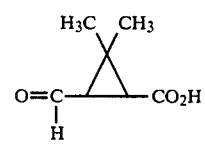

in cis or trans form in the presence of a basic agent, the crude mixture of acids obtained of the formula

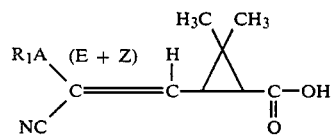

wherein A and R$_1$ have the above definitions, is isolated, from which, if desired, the ΔE and ΔZ isomers are separated, then if necessary, the ΔE and ΔZ acids or their mixtures, as they are or in the form of functional derivatives, are reacted with R$_2$OH alcohols or with a functional derivative of these alcohols, to obtain the esters of formula I in the ΔE or ΔZ form or their mixtures which, if desired, are separated to obtain the ΔE and ΔZ esters.

As basic agent, an example is an alkali metal tert-butylate such as potassium tert-butylate or an organolithium such as butyllithium.

In a preferred mode of the invention to obtain a product of formula I of cis configuration, a dialkyl α-cyano-α-AR$_1$-methylphosphonate is reacted with (1R,5S) 6,6-dimethyl-4(R)-hydroxy-3-oxabicyclo[3.1.0]-hexan-2-one of the formula

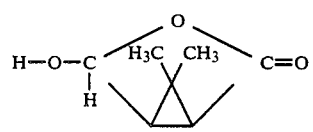

in the presence of potassium tert-butylate, the reaction mixture is acidified to obtain a mixture of crude acids of the formula

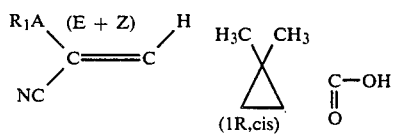

from which, if desired, the ΔE and ΔZ isomers are separated, and then if necessary, the separated isomers or their mixture are reacted as they are or in the form of functional derivatives with an R₂OH alcohol or with a functional derivative of this alcohol; to obtain a product of formula I of trans configuration, a dialkyl α-cyano-α-AR₁-methylphosphonate is reacted with butyl-lithium and the product obtained is reacted with tert-butyl 1R, trans 2,2-dimethyl-3-formyl-cyclopropane carboxylate of the formula

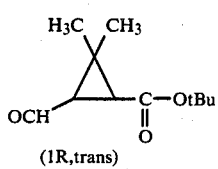

(1R,trans)

the mixture of crude acids of the formula

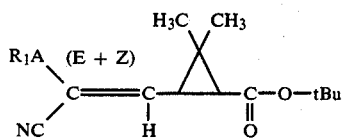

is isolated from which, if desired, the ΔE and ΔZ isomers are separated, then, if desired, the tert-butyl portion is cleaved either by trifluoroacetic acid for the ΔZ isomers or by p-toluene sulfonic acid for the ΔE isomers, and after this, if necessary, the ΔE and ΔZ acids so obtained, or functional derivatives of these acids, are reacted with an R₂OH alcohol or a functional derivative of this alcohol to obtain the corresponding compound of formula I. The separation of the crude acid mixtures to obtain the "ΔE" and "ΔZ" derivatives is carried out by chromatography.

The phosphonates used as starting products are generally known and can be prepared by the process described by Watt in J. Org. Chem., Vol. 41, 28 46 (1976). Certain phosphonates are new and are themselves an object of the present invention, namely: 2-(cyano-2-propyloxymethyl)-2-oxo-4,5-dimethyl-1,3,2-dioxa-phospholane and 2-(cyanoethoxymethyl)-2-oxo-4,5-dimethyl-1,3,2-dioxa-phospholane.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The insecticidal compositions of the invention are particularly preferred and may contain 0.005 to 10% by weight of the active ingredient. Among the preferred notable insecticidal compositions of the invention are those wherein the active compound is selected from the group consisting of (S)α-cyano-3-phenoxybenzyl (1R,cis,ΔE) 3-(2-methoxy-2-cyanoethenyl)-2,2-dimethylcyclopropane carboxylate, (S)α-cyano-3-phenoxybenzyl (1R,cis,ΔZ) 3-(2-methoxy-2-cyanoethenyl)-2,2-dimethyl-cyclopropane carboxylate, (S)α-cyano-3-phenoxy-4-fluorobenzyl (1R,cis,ΔZ) 3-(2-methoxy-2-cyanoethenyl)-2,2-dimethyl-cyclopropane carboxylate, (2,3,4,5,6-pentafluorobenzyl) (1R,cis,ΔZ) 3-(2-methoxy-2-cyanoethenyl)-2,2-dimethyl-cyclopropane carboxylate and (S)α-cyano-3-phenoxy-benzyl (1R,trans,ΔE) 3-(2-methoxy-2-cyanoethenyl)-2,2-dimethyl-cyclopropane carboxylate.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 25% by weight, preferably.

In the case of a serpentine insecticide, the inert support may be made, for example, of pyrethrum marc, Tabu powder (or *Machilus thumbergii* leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of formula I in the oil is preferably 0.03 to 25% by weight.

The compositions of the invention are also useful to combat acariens and nematode parasites of vegetables containing at least one compound of formula I as the active ingredient and they may be in the form of powders, granules, suspensions, emulsions or solutions.

For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

The compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The products of formula I have the advantages of being very photostable and not being toxic to mammals. The various properties of the compounds of formula I correspond perfectly to those required for modern agrochemical use permitting the protection of crops without damage to the environment.

The compositions of the invention are also useful to combat acarien parasites of warm-blooded animals such as ticks, especially ticks of Boophilus species, Hyalomnia species, Amblyomnia species and Rhipicephalus species and to combat all sorts of scabies such as sarcoptic scabies, psoroptic scabies and chorioptic scabies. They can also be useful to combat lice and helminthes. The invention also includes compositions intended to combat parasites of warm-blooded animals, especially ticks and gales, containing at least one compound of formula I.

The said medicaments may be administered externally by vaporization, by powdering, by painting or by bathing. For veterinary usage, the compositions may also be administered by painting the dorsal spine by the "pour on" method as well as being administered digestively or parenterally.

When the compositions are to be used to combat parasitic acariens of animals, the active compounds of formula I are very often incorporated into alimentary compositions in association with a nutritive mixture adapted to the animal to be fed. The nutritive mixture will vary depending upon the species of animal but usually contains cereals, sugars and grains, soybean press cake, peanuts and turnsole, meal of animal origin such as fish meal, synthetic amino acids, mineral salts, vitamins and antioxidants.

Another feature of the invention are insecticidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthalimidomethyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimidomethyl alcohol, 5-benzyl-3-furyl-methyl alcohol, 3-phenoxy-benzyl alcohol or α-cyano-3-phenoxybenzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

To increase the biological activity of the compositions of the invention, classical synergists may be incorporated therein such as 1-(2,5,8-trioxadodecyl)-2-propyl-4,5-methylenedioxybenzene (piperonyl butoxide) or N-(2-ethyl-heptyl)-bicyclo-[2,2-]-5-heptene-2,3-dicarboximide or piperonyl-bis-2-(2'-n-butoxyethoxy)-ethyl acetal (tropital).

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(1R,cis,ΔZ) 3-(2-methoxy-2-cyanoethenyl)-2,2-dimethyl-cyclopropane-carboxylic acid and (1R,cis,ΔE) 3-(2-methoxy-2-cyanoethenyl)-2,2-dimethyl-cyclopropane carboxylic acid 10.35 g of diethyl α-cyano-α-methoxymethylphosphonate and 7.1 g of (1R,5S) 6,6-dimethyl-4(R)-hydroxy-3-oxabicyclo-[3-1-0]hexane-2-one were introduced into 140 ml of tetrahydrofuran and then, at −60° C. and over about 30 minutes, 11.2 g of potassium tert-butylate in 75 ml of tetrahydrofuran were added thereto. The reaction mixture was stirred for 6 hours at −60° C. and then was poured into ice water. The mixture was acidified to a pH of 5 by adding 2N aqueous hydrochloric acid solution and then was extracted with ethyl ether. The extract was evaporated to dryness under reduced pressure and the residue was chromatographed over silica gel. Elution with a mixture of hexane and ethyl acetate (4/6) yielded 738 mg of (1R,cis,ΔZ) 3-(2-methoxy-2-cyanoethenyl)-2,2-dimethyl-cyclopropane carboxylic acid melting at 74° C., then 82° C. and 2.88 g of (1R,cis,ΔE) 3-(2-methoxy-2-cyanoethenyl)-2,2-dimethyl-cyclopropane carboxylic acid melting at 82° C. and 3.74 g of a mixture of "ΔE" and "ΔZ" isomers.

Isomer "ΔZ"

NMR Spectrum (deuterochloroform): Peaks at 1.27–1.28 ppm (hydrogens of geminal methyls); at 1.83–1.97 ppm and 2.2–2.34; 2.37–2.51 ppm (hydrogens in positions 1 and 3 of the cyclopropyl); at 3.8 ppm (hydrogens of methyl of methoxy); at 5.9–6.07 ppm (ethylene hydrogen).

UV Spectrum (ethanol): maximum at 239–240 nm, ε=18.400.

Isomer "ΔE

NMR Spectrum (deuterochloroform): Peaks at 1.3 ppm (hydrogens of geminal methyls); at 1.82–1.96 ppm and 2.05–2.21–2.37 ppm (hydrogens in positions 1 and 3 of cyclopropyl); at 3.68 ppm (hydrogens of methyl of methoxy); at 5.9–6.09 ppm (ethylene hydrogen).

UV Spectrum (ethanol): maximum at 240–241 nm, ε=12,500.

EXAMPLE 2

Tert.-butyl (1R,trans,ΔE) 3-(2-methoxy-2-cyanoethenyl)-2,2-dimethyl-cyclopropane carboxylate and tert-butyl (1R,trans,ΔZ) 3-(2-methoxy-2-cyanoethenyl)-2,2-dimethyl-cyclopropane carboxylate 10.36 g of diethyl α-cyano-α-methoxymethylphosphonate dissolved in 100 ml of tetrahydrofuran were admixed at −60° C. over about 30 minutes with 33 ml of a 15% solution of butyllithium in hexane titrating 1.6 mol/l. and the mixture was stirred for 10 minutes at −60° C. to obtain solution A.

The said solution A was admixed with a solution of 9.9 g of tert-butyl 2,2-dimethyl-3-formylcyclopropane-1-carboxylate in 50 ml of tetrahydrofuran at −60° C. over about 40 minutes and after stirring for 5 hours at −60° C., the reaction mixture was poured into iced water. The mixture was extracted with ether and the ether extract was evaporated to dryness under reduced pressure. The residue was chromatographed over silica gel and eluted with a mixture of hexane and ethyl acetate (95/5) to obtain a 2.98 g of tert-butyl (1R,trans,ΔZ)

3-(2-methoxy-2-cyanoethenyl)-2,2-dimethylcyclopropane carboxylate melting at 57° C. and 7.8 g of tert-butyl (1R,trans,ΔE) 3-(2-methoxy-2-cyanoethenyl)-2,2-dimethyl-cyclopropane carboxylate in the form of oil.

Isomer "ΔZ"

NMR Spectrum (deuterochloroform): Peaks at 1.18–1.27 ppm (hydrogens of geminal methyls); at 1.48 ppm (hydrogens of methyls of tert-butyl); at 3.8 ppm (hydrogens of methyl of methoxy); at 5.2–5.37 ppm (ethylene hydrogen).

UV Spectrum (ethanol): maximum at 239 nm $E_1^1 = 686$, $\epsilon = 17.300$.

Isomer "ΔE"

NMR Spectrum (deuterochloroform): Peaks at 1.17–1.3 ppm (hydrogens of geminal methyls); at 1.48 ppm (hydrogens of methyls of tert-butyl); at 3.67 ppm (hydrogens of $CH_3O$—); at 5.28–5.43 ppm (ethylene hydrogen).

UV Spectrum (ethanol): maximum at 240 nm $E_1^1 = 470$, $\epsilon = 11,800$.

EXAMPLE 3

(1R,trans ΔZ) 3-(2-methoxy-2-cyanoethenyl)-2,2-dimethyl-cyclopropane carboxylic acid 3 g of tert-butyl (1R,trans ΔZ) 3-(2-methoxy-2-cyanoethenyl)-2,2-dimethyl-cyclopropane carboxylate were dissolved in 60 ml of methylene chloride and 14.6 ml of trifluoroacetic acid were introduced slowly at 0° C. with stirring for 3 hours at 0° C. The mixture was evaporated to dryness by distillation under reduced pressure and cyclohexane was added to the residue. The mixture was again evaporated to dryness under reduced pressure and the residue was chromatographed over silica gel. Elution with a mixture of hexane and ethyl acetate (4/6) yielded 2.05 g of (1R,trans,ΔZ) 3-(2-methoxy-2-cyanoethenyl)-2,2-dimethyl-cyclopropane carboxylic acid melting at 110° C.

EXAMPLE 4

(1R,trans,ΔE) 3-(2-methoxy-2-cyanoethenyl)-2,2-dimethyl-cyclopropane carboxylic acid 5 g of tert-butyl (1R,trans,ΔE) 3-(2-methoxy-2-cyanoethenyl)-2,2-dimethyl-cyclopropane carboxylate were dissolved in 50 ml of toluene and after 0.5 g of p-toluene sulfonic acid were added thereto, the reaction mixture was refluxed for 45 minutes, then cooled. The mixture was evaporated to dryness under reduced pressure and water and ether were added to the residue. After stirring, the decanted organic phase was evaporated to dryness under reduced pressure to obtain 3.8 g of (1R,trans,ΔE) 3-(2-methoxy-2-cyanoethenyl)-2,2-dimethyl-cyclopropane carboxylic acid melting at 125° C.

EXAMPLE 5

(1R,cis,ΔZ) 3-(2-ethoxy-2-cyanoethenyl)-2,2-dimethyl-cyclopropane carboxylic acid and (1R,cis,ΔE) 3-(2-ethoxy-2-cyanoethenyl)-2,2-dimethyl-cyclopropane carboxylic acid 1.93 g of lithium bromide were introduced into 14 ml of tetrahydrofuran and then at −30° C., 1.4 ml of diisopropylamine and 1.42 g of (1R,5S) 6,6-dimethyl-4(R)-hydroxy-3-oxabicyclo[3-1-0]-hexan-2-one in 10 ml of tetrahydrofuran and 2.19 g of 2-(cyanoethoxy)-methyl-2-oxo-4,5-dimethyl-1,3,2-dioxapholane were introduced. After stirring for 30 minutes at −30° C., a solution of 2.24 g of potassium tert-butylate in 15 ml of tetrahydrofuran was added with and the mixture was stirred for 2 hours at −15° C. The reaction mixture was then poured into a 2N aqueous solution of hydrochloric acid and was extracted with ether. The ether extract was washed with water and evaporated to dryness under reduced pressure. The residue was chromatographed over silica gel and eluted with a mixture of hexane and ethyl acetate (4/6) then with a mixture of hexane and ethyl acetate (8/2) with 1% of acetic acid to obtain 430 mg of (1R,cis,ΔZ acid) and 560 mg of (1R,cis,ΔE acid).

Isomer Z

NMR Spectrum (deuterochloroform): Peaks at 1.29–1.31 ppm (hydrogens of geminal methyls); at 1.3–1.33–1.45 ppm (hydrogens of ethoxymethyl); at 1.81–2.5 ppm (hydrogens in position 1 and 3 of cyclopropane); at 3.85–3.98–4.1–4.2 ppm (hydrogens of ethoxy methyl); at 5.86–6.03 ppm (ethylene hydrogen).

Isomer E

NMR Spectrum (deuterochloroform): Peaks at 1.2–1.32–1.35 ppm (hydrogens of ethoxy methyl); at 1.28 ppm (hydrogens of geminal methyls); at 1.8–2.33 ppm (hydrogens in positions 1 and 3 of cyclopropane); at 3.7–3.8–3.9–4.05 ppm (hydrogens of ethoxy methylene); at 5.9–6.1 ppm (ethylene hydrogen).

The 2-(cyanoethoxy)-methyl-2-oxo-4,5-dimethyl-1,3,2-dioxapholane used as starting product was prepared as follows by mixing 26.11 g of α-bromo-α-ethoxyacetonitrile and 24.22 g of 2-methoxy-4,5-dimethyl-1,3,2-dioxapholane together and heating slowly at 100° C. and holding there for one hour. After cooling and rectifying under reduced pressure, 27.5 g of 2-(cyanoethoxy)-methyl-2-oxo-4,5-dimethyl-1,3,2-dioxapholane were obtained with a boiling point of 151° C. at 0.4 mm of mercury.

EXAMPLE 6

Mixture of (1R,cis,ΔZ) 3-[2-(2-isopropyloxy)-2-cyano-ethenyl]-2,2-dimethyl-cyclopropane carboxylic acid and (1R,cis,ΔE) 3-[2-(2-isopropyloxy)-2-cyano-1-ethenyl]-2,2-dimethyl-cyclopropane-carboxylic acid 33.1 g of lithium bromide were introduced into 330 ml of tetrahydrofuran at −30° C. and 14 ml of diisopropylamine were added thereto. After stirring for 30 minutes at −30° C., 23.76 g of 2-(cyano-2-isopropyloxymethyl)-2-oxo-4,5-dimethyl-1,3,2-dioxapholane and 14.24 g of (1R,5S) 6,6-dimethyl-4(R)-hydroxy-3-oxabicyclo-[3,1,0]-hexan-2-one were introduced over 20 minutes at −30° C. and after stirring for 30 minutes at −30° C., a solution of 22.55 g of potassium tert-butylate in 220 ml of tetrahydrofuran were introduced over a period of about 30 minutes at −30° C. The mixture was stirred for 3 hours at −20° C. and was then poured into a 2N aqueous solution of hydrochloric acid and extracted with ethyl ether. After washing the ether extract with water, it was evaporated to dryness under reduced pressure and the residue was chromatographed over silica gel. Elution with a mixture of hexane and ethyl acetate (4/6) yielded 14.49 g of mixture of (1R,cis,ΔZ) 3-[2-(2-isopropyloxy)-2-cyano-1-ethenyl]-2,2-dimethylcyclopropane carboxylic acid and (1R,cis,ΔE) 3-[2-(2-isopropyloxy)-2-cyano-1-ethenyl]-2,2-dimethyl-cyclopropane carboxylic acid.

NMR Spectrum (deuterochloroform): Peaks at 1.22–1.35 ppm (hydrogens of geminal methyls); at 1.8–2.5 ppm (hydrogens in position 1 and 3 of cyclopropane); at 4.0–4.7 ppm (hydrogen of >CH of isopropyl); at 5.97–6.13 and 6.10–6.26 ppm (ethylene hydrogen). The data of this spectrum corresponds to a ratio of 55/45 of the two isomers.

2-(cyano-2-isopropyloxymethyl)-2-oxo-4,5-dimethyl-1,3,2-dioxaphospholane 24.47 g of α-bromo-α-isopropyloxyacetonitrile and 20.63 g of 2-methoxy-4,5-dimethyl-1,3,2-dioxaphospholane were mixed together and the reaction mixture was held at 100° C. for one hour and cooled. After rectifying under reduced pressure, 23.76 g of 2-(cyano-2-propyloxy)-methyl-2-oxo-4,5-dimethyl-1,3,2-dioxaphospholane were obtained with a boiling point of 130° C. at 0.3 mm of mercury.

EXAMPLE 7

(1R,cis,ΔE) and (1R,cis,ΔZ) 3-[-2-tert-butyloxy-2-cyanoethenyl]-2,2-dimethyl-cyclopropane carboxylic acid Using the procedure of Example 6, 1R,cis 6,6-dimethyl-4(R)-hydroxy-3-oxabicyclo[3,1,0]-hexan-2-one and diethyl α-cyano-α-tert-butoxymethylphosphonate were reacted to obtain a mixture of (1R,cis,ΔE) and (1R,cis,ΔZ) 3-[2-tert-butyloxy-2-cyanoethenyl]-2,2-dimethyl-cyclopropane carboxylic acid.

EXAMPLE 8

3-phenoxy-benzyl (1R,cis,ΔZ) 3-(2-methoxy-2-cyanoethenyl)-2,2-dimethyl-cyclopropane carboxylate A solution of 750 mg of dicyclohexylcarbodiimide in 2 ml of methylene chloride was added at 0° C. to a mixture of 690 mg of (1R,cis,ΔZ) 3-(2-methoxy-2-cyanoethenyl)-2,2-dimethyl-cyclopropane carboxylic acid, 7 ml of methylene chloride, 700 mg of 3-phenoxy-benzyl alcohol and 30 mg of 4-dimethylamino-pyridine mixed together. After stirring for 3 hours at 20° C., the mixture was concentrated to dryness by distilling under reduced pressure and filtered. The residue was chromatographed over silica gel and eluted with a mixture of hexane and ethyl acetate (8/2) to obtain 1.2 g of 3-phenoxy-benzyl (1R,cis,ΔZ) 3-(2-methoxy-2-cyanoethenyl)-2,2-dimethyl-cyclopropane carboxylate with a specific rotation of $[\alpha]_D = -20° \pm 1°$ (c=1.2% in chloroform).

EXAMPLES 9 TO 42

Using the procedure of Example 8, starting with acids with the formula

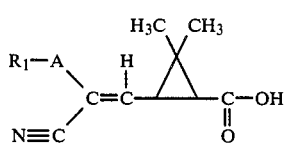

and with alcohols with the formula R₂OH, the following esters of formula I were obtained:

EXAMPLE 9

(S)α-cyano-3-phenoxy-benzyl (1R,cis,ΔE) 3-(2-methoxy-2-cyanoethenyl)-2,2-dimethyl-cyclopropane carboxylate.

EXAMPLE 10

(S)α-cyano-3-phenoxy-benzyl (1R,cis,ΔZ) 3-(2-methoxy-2-cyanoethenyl)-2,2-dimethyl-cyclopropane carboxylate.

EXAMPLE 11

(S)α-cyano-3-phenoxy-4-fluoro-benzyl (1R,cis,ΔE) 3-(2-methoxy-2-cyanoethenyl)-2,2-dimethyl-cyclopropane carboxylate.

EXAMPLE 12

(S)α-cyano-3-phenoxy-4-fluoro-benzyl (1R,cis,ΔZ) 3-(2-methoxy-2-cyanoethenyl)-2,2-dimethyl-cyclopropane carboxylate.

EXAMPLE 13

(R,S)α-cyano-(6-phenoxy-2-pyridyl)-methyl (1R,cis,ΔZ) 3-(2-methoxy-2-cyanoethenyl)-2,2-dimethyl-cyclopropane carboxylate.

EXAMPLE 14

Pentafluorobenzyl (1R,cis,ΔZ) 3-(2-methoxy-2-cyanoethenyl)-2,2-dimethyl-cyclopropane carboxylate.

EXAMPLE 15

S-allethrolone (1R,cis,ΔZ) 3-(2-methoxy-2-cyanoethenyl)-2,2-dimethyl-cyclopropane carboxylate.

EXAMPLE 16

S-allethrolone (1R,cis,ΔE) 3-(2-methoxy-2-cyanoethenyl)-2,2-dimethyl-cyclopropane carboxylate.

EXAMPLE 17

1-(2-propynyl)-2,4-dioxoimidazolidin-3-yl-methyl (1R,cis,ΔZ) 3-(2-methoxy-2-cyanoethenyl)-2,2-dimethyl-cyclopropane carboxylate.

EXAMPLE 18

(6-phenoxy-2-pyridyl)-methyl (1R,cis,ΔZ) 3-(2-methoxy-2-cyanoethenyl)-2,2-dimethyl-cyclopropane carboxylate.

EXAMPLE 19

(6-phenoxy-2-pyridyl)-methyl (1R,cis,ΔE) 3-(2-methoxy-2-cyanoethenyl)-2,2-dimethyl-cyclopropane carboxylate.

EXAMPLE 20

(R)α-ethynyl-3-phenoxy-benzyl (1R,cis,ΔE) 3-(2-methoxy-2-cyanoethenyl)-2,2-dimethyl-cyclopropane carboxylate.

EXAMPLE 21

(R)α-ethynyl-3-phenoxy-benzyl(1R,cis,ΔZ) 3-(2-methoxy-2-cyanoethenyl)-2,2-dimethyl-cyclopropane carboxylate.

EXAMPLE 22

(R)3-phenoxyphenethyl (1R,cis,ΔE) 3-(2-methoxy-2-cyanoethenyl)-2,2-dimethyl-cyclopropane carboxylate.

EXAMPLE 23

(R)3-phenoxyphenethyl (1R,cis,ΔZ) 3-(2-methoxy-2-cyanoethenyl)-2,2-dimethyl-cyclopropane carboxylate.

EXAMPLE 24

(S)α-cyano-3-phenoxy-benzyl(1R,trans,ΔE) 3-(2-methoxy-2-cyanoethenyl)-2,2-dimethyl-cyclopropane carboxylate.

EXAMPLE 25

(S)α-cyano-3-phenoxy-benzyl(1R,trans,ΔZ) 3-(2-methoxy-2-cyanoethenyl)-2,2-dimethyl-cyclopropane carboxylate.

EXAMPLE 26

(S)α-cyano-3-phenoxy-4-fluorobenzyl (1R,trans,ΔE) 3-(2-methoxy-2-cyanoethenyl)-2,2-dimethyl-cyclopropane carboxylate.

EXAMPLE 27

(S)α-cyano-3-phenoxy-4-fluorobenzyl (1R,trans,ΔZ) 3-(2-methoxy-2-cyanoethenyl)-2,2-dimethyl-cyclopropane carboxylate.

EXAMPLE 28

(S)α-cyano-3-phenoxy-benzyl(1R,cis,ΔE) 3-(2-ethoxy-2-cyanoethenyl)-2,2-dimethyl-cyclopropane carboxylate.

EXAMPLE 29

(S)α-cyano-3-phenoxy-benzyl(1R,cis,ΔZ) 3-(2-ethoxy-2-cyanoethenyl)-2,2-dimethyl-cyclopropane carboxylate.

EXAMPLE 30

(S)α-cyano-3-phenoxy-4-fluorobenzyl (1R,cis,ΔZ) 3-(2-ethoxy-2-cyanoethenyl)-2,2-dimethyl-cyclopropane carboxylate.

EXAMPLE 31

(R,S)α-cyano (6-phenoxy-2-pyridyl)-methyl (1R,cis,ΔZ) 3-(2-ethoxy-2-cyanoethenyl)-2,2-dimethyl-cyclopropane carboxylate.

EXAMPLE 32

(S)α-cyano-3-phenoxy-benzyl(1R,cis,ΔE) 3-(2-isopropoxy-2-cyanoethenyl)-2,2-dimethyl-cyclopropane carboxylate.

EXAMPLE 33

(S)α-cyano-3-phenoxy-benzyl (1R,cis,ΔZ) 3-(2-isopropoxy-2-cyanoethenyl)-2,2-dimethyl-cyclopropane carboxylate.

EXAMPLE 34

(S)α-cyano-3-phenoxy-4-fluorobenzyl (1R,cis,ΔE) 3-(2-isopropoxy-2-cyanoethenyl)-2,2-dimethyl-cyclopropane carboxylate.

EXAMPLE 35

(S)α-cyano-3-phenoxy-4-fluorobenzyl (1R,cis,ΔZ) 3-(2-isopropoxy-2-cyanoethenyl)-2,2-dimethyl-cyclopropane carboxylate.

EXAMPLE 36

(RS)α-cyano-(6-phenoxy-2-pyridyl)-methyl (1R,cis,ΔE) 3-(2-isopropoxy-2-cyanoethenyl)-2,2-dimethyl-cyclopropane carboxylate.

EXAMPLE 37

(RS)α-cyano (6-phenoxy-2-pyridyl)-methyl (1R,cis,ΔZ) 3-(2-isopropoxy-2-cyanoethenyl)-2,2-dimethyl-cyclopropane carboxylate.

EXAMPLE 38

(S)α-cyano-3-phenoxy-benzyl (1R,cis,ΔE) 3-(2-terbutoxy-2-cyanoethenyl)-2,2-dimethyl-cyclopropane carboxylate.

EXAMPLE 39

(S)α-cyano-3-phenoxy-benzyl (1R,cis,ΔZ) 3-(2-terbutoxy-2-cyanoethenyl)-2,2-dimethyl-cyclopropane carboxylate.

EXAMPLE 40

(S)(α)-cyano-3-phenoxy-4-fluorobenzyl (1R,cis,ΔE) 3-(2-terbutoxy-2-cyanoethenyl)-2,2-dimethyl-cyclopropane carboxylate.

EXAMPLE 41

(S)α-cyano-3-phenoxy-4-fluorobenzyl (1R,cis,ΔZ) 3-(2-terbutoxy-2-cyanoethenyl)-2,2-dimethyl-cyclopropane carboxylate.

EXAMPLE 42

(R)α-cyano-(6-phenoxy-2-pyridyl)-methyl (1R,cis,-ΔE+Z) 3-(2-terbutoxy-2-cyanoethenyl)-2,2-dimethyl-cyclopropane carboxylate.

| Example | A | $R_1$ | Δ | Configuration | $R_2$ | Melting Point | $α_D$ | Concentration in $CHCl_3$ |
|---|---|---|---|---|---|---|---|---|
| 9 | O | $CH_3$ | E | 1R, cis | 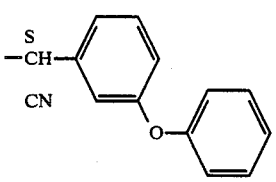 | 76° C. | +45° | 1% |
| 10 | " | " | Z | " | " | — | +27° | 0,5% |

-continued

| Example | A | R₁ | Δ | Configuration | R₂ | Melting Point | αD | Concentration in CHCl₃ |
|---|---|---|---|---|---|---|---|---|
| 11 | " | " | E | " | 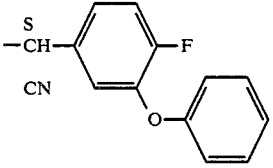 -CH(S)(CN)-C₆H₃(F)(OC₆H₅) | — | +46,5° | 0,7% |
| 12 | " | " | Z | " | " | — | +36° | 0,8% |
| 13 | " | " | Z | " | 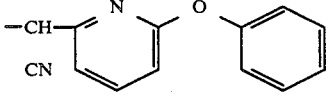 -CH(CN)-pyridyl-OC₆H₅ | — | 0° | 1% |
| 14 | " | " | Z | " | pentafluorobenzyl | — | | |
| 15 | " | " | Z | " | S—allethrolone | — | +14,5° | 0,6% |
| 16 | " | " | E | " | " | — | +65° | 0,5% |
| 17 | " | " | Z | " | 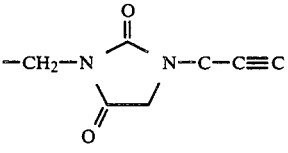 -CH₂-N(CO)₂N-C-C≡C | — | | |
| 18 | " | " | Z | " |  -CH₂-pyridyl-OC₆H₅ | — | -2,5° | 0,6% |
| 19 | " | " | E | " | " | — | +51° | 0,6% |
| 20 | " | " | E | " | 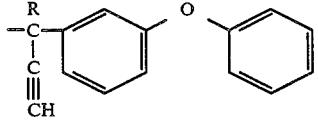 -C(R)(C≡CH)-C₆H₄-OC₆H₅ | — | +45° | 0,75% |
| 21 | " | " | Z | " | " | — | +8,5° | 1% |
| 22 | " | " | E | " | 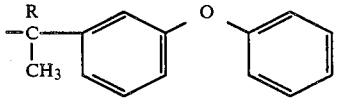 -C(R)(CH₃)-C₆H₄-OC₆H₅ | — | +125,5° | 0,65% |
| 23 | " | " | Z | " | " | — | +121,5° | 0,8% |
| 24 | " | " | E | 1R, trans | 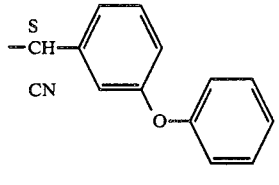 -CH(S)(CN)-C₆H₄-OC₆H₅ | — | -5,5° | 1,4% |
| 25 | " | " | Z | " | " | — | 0° | |
| 26 | " | " | E | " | 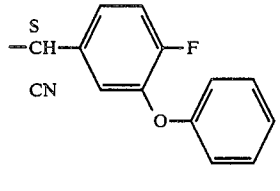 -CH(S)(CN)-C₆H₃(F)(OC₆H₅) | 107° | -6,5° | 1,7% |
| 27 | " | " | Z | " | " | — | +2° | 0,4% |

-continued

| Example | A | R₁ | Δ | Configuration | R₂ | Melting Point | αD | Concentration in CHCl₃ |
|---|---|---|---|---|---|---|---|---|
| 28 | " | C₂H₅ | E | 1R, cis | -CH(S)(CN)-C₆H₄-O-C₆H₅ | — | +41° | 0,7% |
| 29 | " | " | Z | " | " | — | +38° | 0,7% |
| 30 | " | —CH₂—CH₃ | Z | " | -CH(S)(CN)-C₆H₃(F)-O-C₆H₅ | — | +41,5° | 0,6% |
| 31 | " | " | Z | " | -CH(CN)-pyridine(N,O)-O-C₆H₅ | — | +5° | 0,5% |
| 32 | " | CH(CH₃)₂ | E | " | -CH(S)(CN)-C₆H₄-O-C₆H₅ | — | +51° | 1% |
| 33 | " | " | Z | " | " | 92° | +50,5° | 0,5% |
| 34 | " | " | E | " | -CH(S)(CN)-C₆H₃(F)-O-C₆H₅ | — | +56,5° | 0,6% |
| 35 | " | " | Z | " | " | — | +43,5° | 0,7% |
| 36 | " | " | E | " | -CH(CN)-pyridine(N,O)-O-C₆H₅ | — | +49,5° | 0,5% |
| 37 | " | " | Z | " | " | — | +26,5° | 0,5% |
| 38 | " | C(CH₃)₃ | E | " | -CH(S)(CN)-C₆H₄-O-C₆H₅ | 72° | +64° | 0,5% |
| 39 | " | " | Z | " | " | — | +40° | 0,5% |
| 40 | " | " | E | " | -CH(S)(CN)-C₆H₃(F)-O-C₆H₅ | — | +61° | 0,5% |
| 41 | " | " | Z | " | " | — | +39° | 0,5% |

-continued

| Example | A | R₁ | Δ Configuration | R₂ | Melting Point | $\alpha_D$ | Concentration in $CHCl_3$ |
|---|---|---|---|---|---|---|---|
| 42 | " | " | E + Z | " 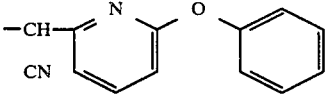 | — | +26,5° | 0,6% |

To prepare the geometrical isomers of Examples 9 and 42, starting with the pure E or Z acid the corresponding E or Z esters were obtained; starting with E + Z acid, a mixture of esters of E + Z was obtained which was separated by physical processes such as chromatography.

EXAMPLE 43

Soluble concentrate

A homogeneous mixture of 0.25 g of the product of Example 9, 1.00 g of piperonyl butoxide, 0.25 g of Tween 80, 0.1 g of Topanol A and 98.4 g of water was prepared.

EXAMPLE 44

Emulsifiable concentrate

An intimate mixture of 0.015 g of product of Example 14, 0.5 g of piperonyl butoxide, 0.1 g of Topanol A and 99.385 g of xylene was prepared.

EXAMPLE 45

Emulsifiable concentrate

A homogeneous mixture of 1.5 g of product of Example 12, 20.00 g of Tween 80, 0.1 g of Topanol A and 78.4 g of xylene was prepared.

EXAMPLE 46

Fumigating composition

An intimate mixture of 0.25 g of the product of Example 10, 25 g of Tabu powder, 40 g of cedar leaf powder, 33.75 g of pine wood powder, 0.5 g of Brilliant green and 0.5 g of p-nitrophenol was prepared.

Insecticidal Activity (A) Knock-down effect on house flies

The test insects were 4 day old female house flies and atomization was effected directly at a concentration of 0.25 g/l into a Kearns and March chamber using as solvent a mixture of acetone (5%) and Isopar L (petroleum solvent) with a quantity of solvent used 2 ml per second. Reading were made every minute for 10 minutes and then at 15 minutes to determine $KT_{50}$ by the usual methods. The results obtained are summarized in the following Table.

| Product of Example | $KT_{50}$ |
|---|---|
| 9 | 2.12 |
| 10 | 2.29 |
| 24 | 1.85 |
| 12 | 2.45 |
| 14 | 1.91 |

(B) Lethal effect on various insects (A) Study of the lethal effect on cockroaches The tests were carried out by contact on a film on glass formed by depositing acetone solutions of different concentrations on the bottom of a glass Petri dish with a pipette and edges of the dish were previously talced to prevent the insects from escaping. The lethal concentration ($LC_{50}$) was determined and the results obtained are summarized in the following table:

| Product of Example | $LC_{50}$ in mg/m² |
|---|---|
| 9 | 3.4 |
| 10 | 0.50 |
| 24 | 4.0 |
| 12 | 0.38 |
| 14 | 1.91 |

(B) Lethal effect on larvae of *Spodoptera littoralis*

The tests were carried out by topical application of an acetone solution with an Arnold micro-manipulator on the dorsal thorax of the larvae and 15 larvae were used per dose of the product under test. The larvae used were larvae of the fourth larval stage, that is to say, aged about 10 days when they were bred at 24° C. and 65% relative humidity. After treatment, the individuals were placed on an artifical nutritive medium (Poitout medium) and mortality checks were made 48 hours after treatment. The results obtained are summarized in the following table:

| Product of Example | $LD_{50}$ in ng/per insect |
|---|---|
| 9 | 10.0 |
| 10 | 1.03 |
| 24 | 19.7 |
| 12 | 2.79 |
| 14 | 24.1 |

(C) Lethal effect on *Aphis cracivora*

Adults were used after 7 days and 10 Aphis were used per concentration with a contact-ingestion method. The treatment was carried out with a Fisher pistol on a bean leaf which was placed in a plastic Petri dish on a disc of moistened paper. The treatment was carried out with 2 ml of an acetone solution of the product under test with 1 ml per face of the leaf. The infestation by the insects was done after drying of the leaf, and the insects were kept in contact with the leaf for one hour. The insects were then placed on untreated leaves and the mortality was checked after 24 hours. The results obtained are summarized in the following table.

| Product of Example | $LD_{50}$ in ng per insect |
|---|---|
| 10 | 0.69 |
| 12 | 2.62 |
| 14 | 5.15 |

Various modifications of the products and method of the invention may be made without departing from the spirit or scope thereof and it is to be understood that the invention is intended to be limited only as defined in the appended claims.

What we claim is:

1. A cyclopropane carboxylate in all isomeric forms of the formula

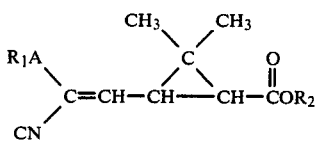

wherein A is selected from the group consisting of —O—, —S—,

and —SO₂—, R₁ is selected from the group consisting of optionally unsaturated alkyl of 1 to 18 carbon atoms optionally containing at least one heteroatom in the carbon chain and optionally substituted with at least one halogen, aryl of 6 to 18 carbon atoms and aralkyl of 7 to 18 carbon atoms and R₂ is selected from the group consisting of

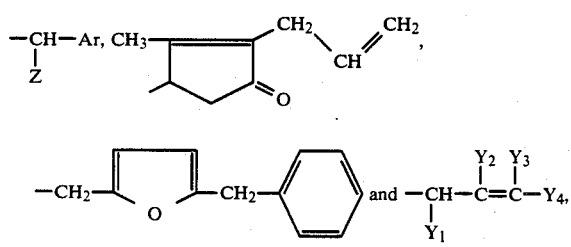

Z is selected from the group consisting of hydrogen, ethynyl and —CN, Ar is selected from the group consisting of phenyl, pentafluorophenyl

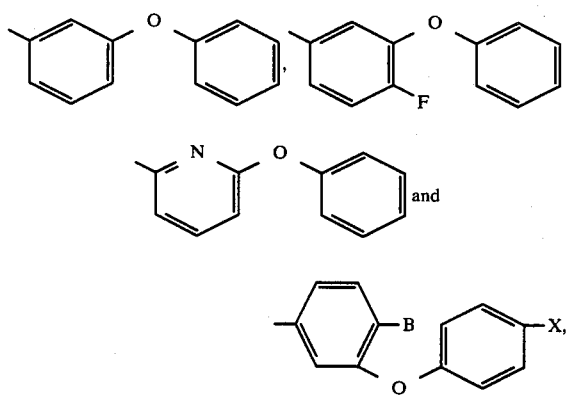

B is hydrogen or fluorine, X is fluorine, chlorine or bromine, Y₁ is selected from the group consisting of hydrogen, fluorine, chlorine, bromine, —C≡N and —C≡CH, Y₂, Y₃ and Y₄ are individually selected from the group consisting of hydrogen, fluorine, chlorine, bromine, alkyl of 1 to 8 carbon atoms and cycloalkyl of 3 to 8 carbon atoms optionally substituted by a functional group selected from the group consisting of halogen, —OH or —SH, —OR', —SR' wherein R' is alkyl of 1 to 8 carbon atoms, —NO₂,

wherein R" and R‴ are individually selected from the group consisting of hydrogen and alkyl of 1 to 8 carbon atoms, —C≡N, —SO₃H, —PO₄H₂, —COAlK₁, —SO₂AlK₂ and —SO₃AlK₃ in which AlK₁, AlK₂ and AlK₃ are alkyl of 1 to 18 carbon atoms, alkenyl of 2 to 8 carbon atoms and alkynyl of 2 to 8 carbons.

2. A compound of claim 1 wherein A is oxygen.

3. A compound of claim 1 having the formula

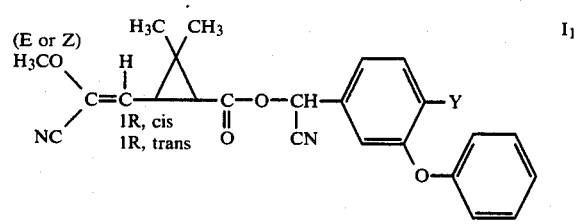

wherein Y is hydrogen or fluorine.

4. A compound of claim 1 having the formula

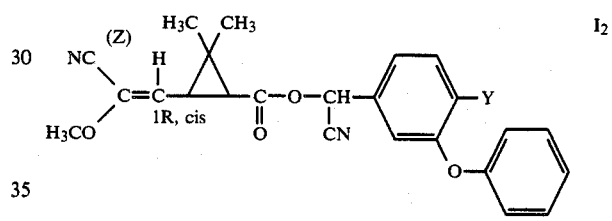

wherein Y is hydrogen or fluorine.

5. A compound of claim 1 selected from the group consisting of (S) α-cyano-3-phenoxy-benzyl(1R,cis,ΔE) 3-(2-methoxy-2-cyanoethenyl)-2,2-dimethyl-cyclopropane carboxylate, (S) α-cyano-3-phenoxy-benzyl (1R,cis ΔZ) 3-(2-methoxy-2-cyanoethenyl)-2,2-dimethyl-cyclopropane carboxylate, (S) α-cyano-3-phenoxy-4-fluorobenzyl (1R,cis ΔZ) 3-(2-methoxy-2-cyanoethenyl)-2,2-dimethyl-cyclopropane carboxylate, 2,3,4,5,6-pentafluorobenzyl (1R,cis ΔZ) 3-(2-methoxy-2-cyanoethenyl)-2,2-dimethyl-cyclopropane carboxylate, (S) α-cyano-3-phenoxybenzyl (1R,trans ΔE) 3-(2-methoxy-2-cyanoethenyl)-2,2-dimethyl-cyclopropane carboxylate.

6. An insecticidal composition comprising an insecticidally effective amount of at least one compound of claim 1 and an inert carrier.

7. A composition of claim 6 wherein A is oxygen.

8. A composition of claim 6 wherein the active compound has the formula

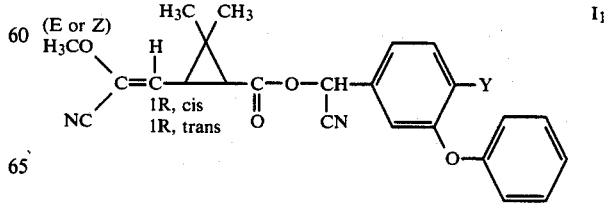

wherein Y is hydrogen or fluorine.

9. A composition of claim 6 wherein the active compound has the formula

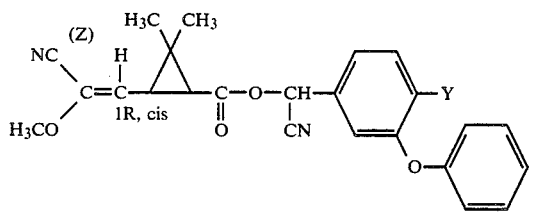

wherein Y is hydrogen or fluorine.

10. A composition of claim 6 wherein the active compound is selected from the group consisting of (S) α-cyano-3-phenoxybenzyl (1R,cis,ΔE) 3-(2-methoxy-2-cyanoethenyl)-2,2-dimethylcyclopropane carboxylate, (S) α-cyano-3-phenoxy-benzyl (1R,cis,ΔZ) 3-(2-methoxy-2-cyanoethenyl)-2,2-dimethyl-cyclopropane carboxylate, (S) α-cyano-3-phenoxy-4-fluorobenzyl (1R,cis,ΔZ) 3-(2-methoxy-2-cyanoethenyl)-2,2-dimethyl-cyclopropane carboxylate, 2,3,4,5,6-pentafluorobenzyl (1R,cis,ΔZ) 3-(2-methoxy-2-cyanoethenyl)-2,2-dimethyl-cyclopropane-carboxylate, (S)α-cyano-3-phenoxybenzyl (1R,trans,ΔE) 3-(2-methoxy-2-cyanoethenyl)-2,2-dimethyl-cyclopropane carboxylate.

11. A method of combatting insects comprising contacting insects with an insecticidally effective amount of at least one compound of claim 1.

12. A method of claim 11 wherein A is oxygen.

13. A method of claim 11 wherein the active compound has the formula

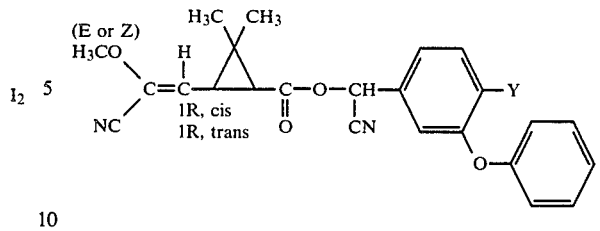

wherein Y is hydrogen or fluorine.

14. A method of claim 11 wherein the active compound has the formula

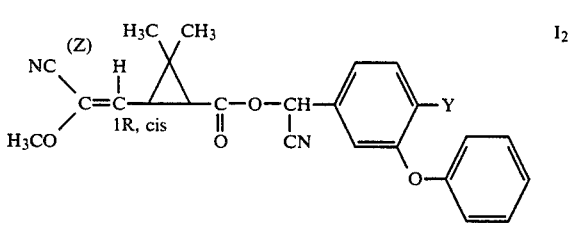

wherein Y is hydrogen or fluorine.

15. A method of claim 11 wherein the active compound is selected from the group consisting of (S) α-cyano-3-phenoxy-benzyl (1R,cis,ΔE) 3-(2-methoxy-2-cyanoethenyl)-2,2-dimethyl-cyclopropane carboxylate, (S) α-cyano-3-phenoxy-benzyl (1R,cis,ΔZ) 3-(2-methoxy-2-cyanoethenyl)-2,2-dimethyl-cyclopropane-carboxylate, (S) α-cyano-3-phenoxy-4-fluorobenzyl (1R,cis,ΔZ) 3-(2-methoxy-2-cyanoethenyl)-2,2-dimethyl-cyclopropane carboxylate, 2,3,4,5,6-pentafluoro-benzyl (1R,cis,ΔZ) 3-(2-methoxy-2-cyanoethenyl)-2,2-dimethyl-cyclopropane-carboxylate, (S) α-cyano-3-phenoxy-benzyl (1R,trans,ΔE) 3-(2-methoxy-2-cyanoethenyl)-2,2-dimethyl-cyclopropane carboxylate.

* * * * *